United States Patent
Quintanilla Almagro et al.

(10) Patent No.: US 7,220,438 B2
(45) Date of Patent: May 22, 2007

(54) **PHARMACOLOGICAL ACTIVITIES OF *CURCUMA LONGA* EXTRACTS**

(75) Inventors: Eliseo Quintanilla Almagro, Alicante (ES); Ana Ramírez Bosca, Alicante (ES); August Bernd, Alicante (ES); José Pardo Zapata, Alicante (ES); Joaquin Diäz Alperi, Alicante (ES); David Pamies Mira, Alicante (ES); Miguel Angel Carrion Gutierrez, Alicante (ES); José Miguel Sempere Ortells, Alicante (ES)

(73) Assignee: Asac Compañia de Biotecnologia, Alicante (ES)

( * ) Notice: Subject to any disclaimer, the term of this patent is extended or adjusted under 35 U.S.C. 154(b) by 460 days.

(21) Appl. No.: 10/684,452

(22) Filed: Oct. 15, 2003

(65) Prior Publication Data

US 2004/0126442 A1 Jul. 1, 2004

Related U.S. Application Data

(63) Continuation-in-part of application No. 09/856,035, filed as application No. PCT/ES00/00354 on Sep. 21, 2000, now Pat. No. 6,841,177.

(30) Foreign Application Priority Data

Sep. 23, 1999 (ES) .................................. 9902364

(51) Int. Cl.
*A61K 36/00* (2006.01)
*A61K 36/906* (2006.01)
(52) U.S. Cl. ...................................... 424/756; 514/863
(58) Field of Classification Search ...................... None
See application file for complete search history.

(56) References Cited

U.S. PATENT DOCUMENTS

| | | | | |
|---|---|---|---|---|
| 5,693,327 A | * | 12/1997 | Shah | ........................... 424/734 |
| 5,891,924 A | | 4/1999 | Aggarwal | |
| 5,935,581 A | * | 8/1999 | Kapadia et al. | .............. 424/773 |
| 6,019,735 A | | 2/2000 | Kensey et al. | |
| 6,440,468 B1 | | 8/2002 | Quintanilla Almagro et al. | |
| 2002/0164374 A1 | | 11/2002 | Jackson et al. | |

FOREIGN PATENT DOCUMENTS

| | | | |
|---|---|---|---|
| DE | 4440112 | * | 5/1996 |
| ES | 2103689 | * | 9/1997 |
| JP | 09143086 | * | 6/1997 |
| JP | 11151309 | * | 8/1999 |

OTHER PUBLICATIONS

Deshpande et al. Cancer Letters. 1997. vol. 118, pp. 79-85.*
Kuttan et al. Cancer Letters. 1985. vol. 29, No. 2, pp. 197-202.*
Paek et al. Archives Pharmacal Research. 1996. vol. 19, No. 2, pp. 91-94.*
Bernd et al. J. Invest. Dermatol. 1997. vol. 109, No. 3, pp. 460. Abstract from the 27th Annual Metting of the European Society for Dermatological Research. KOSMET Abstract enclosed.*
Yegnanarayan et al. Indian J. Medical Research. 1976. vol. 64, No. 4, pp. 601-608, BIOSIS Abstract enclosed.*
Hwang et al. Korean Biochem. J. 1980. vol. 13, No. 1, pp. 25-40, BIOSIS Abstract enclosed.*
Miquel et al, *Age*, 18(4):171-174 (1995).
Srinivas et al, *Archives of Biochem. and Biophys.*, 292(2):617-623 (1992).
Dahl et al, *Photochem. and Photobiol.*, 59(3):290-294 (1994).
Ishizaki et al, *Dermatology*, 193(4):311-317 (1996).
Huang et al, *Eur. J. of Pharmacology*, 221:381-384 (1992).
Simon et al, *Cancer Letters*, 129(1):111-116 (1998).
Yasni et al, *Food Chem. Toxic.*, 31(3):213-218 (1993).
Bosca et al, *Age*, 20(3):165-168 (1997).
Deshpande et al, *Medical Science Research*, 28(10):695-698 (1997).
Quiles et al, *BioFactors*, 8(1-2):51-57 (1998).
Tsuda et al, *Atherosclerosis*, 122(2):226-233 (1996).

* cited by examiner

*Primary Examiner*—Christopher R. Tate
(74) *Attorney, Agent, or Firm*—Sughrue Mion, PLLC (57) ABSTRACT

This invention concerns to a topical pharmaceutical composition comprising an water soluble *Curcuma* extract, and suitable excipients for said topical administration; the process for obtaining said pharmaceutical compositions; the use of different *Curcuma* extracts as photosensitizing agents for the treatment of proliferative diseases; and the use of *Curcuma* extract or curcuminoids in combination with a radiation for the treatment of proliferative diseases on eukaryote cells.

18 Claims, 8 Drawing Sheets

PHARMACOLOGICAL ACTIVITIES OF *CURCUMA LONGA* EXTRACTS

CROSS-REFERENCE TO RELATED APPLICATION

This application is a Continuation-In-Part of U.S. application Ser. No. 09/856,035, filed Feb. 19, 2002, now U.S. Pat. No. 6,841,177; which in turn is a § 371 of PCT/ES00/00354, filed Sep. 21, 2000. U.S. application Ser. No. 09/856,035 is incorporated by reference herein in its entirety.

TECHNICAL FIELD OF THE INVENTION

This invention concerns to a topical pharmaceutical composition comprising an water soluble *Curcuma* extract, and suitable excipients for said topical administration; the process for obtaining said pharmaceutical compositions; the use of different *Curcuma* extracts as photosensitising agents for the treatment of proliferative diseases; and the use of *Curcuma* extract or curcuminoids in combination with a radiation for the treatment of proliferative diseases on eukaryote cells.

STATE OF THE ART

Psoriasis is a chronic inflammatory dermatitis of unknown aetiology. Clinically, it is characterised by papulous lesions on erythemato-scaly maculae. The majority of these lesions are due to alterations in cellular proliferation marked by immunological and genetic mechanisms, and therefore should be considered as "proliferative disease".

We find an increase in arachinonic acid and its derivatives, both in normal and diseased skin; an increase in polyamines, an increase of B4 leukotriene in the scales. From the epidermis and the dermis we find an increase in Langerhans cells with lower infiltration of CD8 lymphocytes compared with CD4. These patients' neutrophils synthesise double the number of B4 leukotrienes as healthy individuals.

IL-6 interleukin is a cytokine that structures the 2(BSF-2) factor, structurally identical to interferon $\beta$-2(IFN-$\beta$-2). IL-6 is synthesised in the fibroblasts, monocytes and T cells. This cytokine stimulates the acute phase of protein synthesis and the production of immunoglobulins.

IL-8 is an interleukin that is directly involved in psoriasis, since it is responsible for producing the migration of the neutrophils that are produced in the epidermis and consequently increases the inflammatory process.

In the present therapy used for psoriasis it is fundamental to act on cellular proliferation and the production of cytokines by the use of glucocorticoids and/or photosensitising agents (psoralens).

Cell cultures are acknowledged models for the study of cell physiology and the effect of drugs. HaCat cells are derived from human keratinocytes that exhibit the same differentiations as normal keratinocytes. Therefore, HaCat cells are an extraordinary model for testing different substances for topical application.

Keratinocytes are very biologically active cells, the function of which is not only to produce keratin synthesis to form the corneal stratus, but which also have immunological properties based on the production and secretion of cytokines and the selective expression of surface receivers.

Different stimulants including ultraviolet radiation have inflammatory responses that act directly on these keratinocytes, producing a release of cytokines and adhesion molecules. This production of substances on the epidermis level starts the cutaneous inflammation symptoms, releasing the IL-6 and the IL-8, which are two cytokines involved in inflammatory cutaneous processes.

Glucocorticoids are the substances most used in the dermatology field, because of their immunosuppressant and anti-inflammatory properties, manifest after UV radiation, but with no effect in visible light.

Different studies show that corticoids affect the production of pro-inflammatory cytokines. Well-known glucocorticoids such as hydrocortisone-17-butyrate and betametasone-17-valerate produce a decrease in inflammatory cytokines after ultraviolet radiation.

The accessibility of the skin often allows for skin alterations to be treated by the topical application of drugs. Topical corticoids, thanks to their anti-inflammatory, vaso constricting and antimycotic properties, have been seen to be useful in a large variety of dermatosis. Nevertheless, the application of corticoids has a series of side effects that have a direct impact on the skin:

Cutaneous atrophies, which consist of thin, transparent skin, purple lesions, star-shaped scars and elastic catabolic striae.

Delay in scar formation because of inhibition of the fibroblasts' function.

Disguise and de-typing of cutaneous infections, particularly dermatophytosis, making diagnosis difficult and with the possible appearance of viral or bacterial cutaneous infections.

Skin pigmentation disorders with hyper or hypopigmentation.

Contact dermatitis.

Habituation and tachyphylaxis phenomena that require the use of increasingly strong products and lead to relapses with the appearance of increasingly severe forms of the process (pustular psoriasis) that could be caused by suddenly ceasing administration.

Systemic side effects are fortunately less frequent, since the use of corticoids for long periods is required, as for psoriasis. The most common side effects are:

Inhibition of the hypothalamus-hypophysial-suprarenal axis.

Episodes of hyperglucaemia and glucaemia.

A fall in the number of eosinophils.

Clinical manifestations of Cushing's Syndrome.

Other therapies used for psoriasis are the oral or topical application of photosensitising substances (psoralens) together with ultraviolet A radiation. The photochemistry of psoralens is not well-known, and can act on several levels. Psoralens bind with DNA and RNA, but interact with lysosomes, endotheliums, cytoplasmatic membranes and dermic cells. In the dark, psoralen is intercalated between the DNA bases. With UVA, cyclobutane monoadducts are produced by binding with a DNA base thymine or cytokine. If radiation continues, a new photon stimulates the other double psoralen link to form a crossover link with the thymine from the other DNA chain. The formation of these bifunctional adducts suppresses DNA synthesis. Another reaction that is observed is that the photoactivated psoralen can act with molecular oxygen to produce an oxygen singlet, superoxide anion and free radicals, and all these reactive forms act on the keratinocytes. The use of psoralens, therefore, presents side effects that are well known in dermatological literature, such as a decrease in delayed immunity, phototoxic reactions, immunosuppression, a decrease in the production of IL-1 by the keratinocytes and more inclination to skin cancers.

The term "photosensitising substances" means the drugs which their pharmacological activity is enhanced when the drug is administrated in combination of an electromagnetical radiation: UV-A, UV-B, UV-C, or visible light. The photosensitising drugs have been used in the art for the treatment of different diseases with an excess of hyperproliferation such as vitiligo, atopic dermatitis, granuloma annulare, lichen, mycosis fungoides, lymphomas, leukaemia, etc., improving the efficacy of the drug, however these drug in combination of any radiation produce more adverse effects.

Curcumin and the curcuminoids present in the rhizomes of Curcuma, particularly Curcuma longa, and the Zingiberaceae family in general, have been used for the treatment of a large variety of diseases. Examples are U.S. Pat. No. 5,891,924 (inhibitor of NF kappa B activation), U.S. Pat. No. 5,336,496 (inhibitor of delta 5 desaturase), EP 256353 (treatment of bad absorption syndromes), EP 568001 (antiviral agent), U.S. Pat. No. 5,108,750 (hyperlipidaemia and platelet aggregation reducer), FR 2655054 (cell protector) and EP 550807 (antioxidant and anti-inflammatory properties), EP440885 (anti-inflammatory), EP 319058 (against hair loss), U.S. Pat. No. 5,108,750, U.S. Pat. No. 4,906,471 and U.S. Pat. No. 4,842,859 (antiplatelet aggregation and anti-cholesterol agent), WO 88/05304 (treatment of neurological disorders), WO 96/03999 (lipidic peroxide reducer), ES 20103689 (modulates high and low density oxidised lipoproteins, protects keratinocytes against free radicals and increases cell proliferation in aged human tissue).

The aqueous extract of Curcuma longa, free from curcuminoids, has also been seen to have antioxidant properties. Srinivas et al, *Archives of Biochemistry and Biophysics*, 292(2):617–623 (1992), describe the antioxidant activity of turmerin, a protein that is present in Curcuma rhizomes. Yeharayou et al, *Ind. J. Med. Res.*, 64(4):601 (1976), describe the anti-inflammatory effect of the aqueous extract of Curcuma longa, with properties similar to hydrocortisone. Gonda et al, *Chem. Pharm. Bull*, 40:990 (1992), describes the immunological activity of ukonan A and its degradation products.

On the other hand, WO 96/03999 and its patent equivalents, describes a pharmaceutical for oral administration comprising an hydro alcoholic extract of Curcuma and its use as lipidic peroxides reducer. ES-8100878, equivalent to EP 0020274, discloses different cosmetic compositions comprising Curcuma extracts characterized by curcuminoids.

The document that is closest to our invention, Tonnessee et al, *J. Pharm. Sci.*, 76(DEG 5) (1987), describes the phototoxic activity of curcumin in biological systems without nuclei (*E. Coli, Salmonella typhimuis*); however, this document comments on the possible mutagenic effects on DNA.

Dhal et al, *Photochemistry and Photobiology*, 59(3):290 (1994), describe the phototoxic activity with visible light of curcumin on rat cells.

Therefore, the actually used treatment for the treatment of proliferative disease, mainly psoriasis, produces adverse effects in patients, and the photosensitization methods are carry out using an UV radiation producing also adverse effects, concretely mutagenic reactions due to the interactions between the drug and DNA.

The use of the vegetable extracts of plants with pharmacological activities is well-known, and it is known that the active ingredients can be isolated and purified from plant extracts. However, active ingredients that are purified and/or synthetically obtained could have side effects or be toxic, such as in the case of atropine, digitalis, nicotine etc.

Vegetable extracts contain a series of structurally related chemical species due to the metabolic processes in plants. These related compounds could have a synergic effect on pharmacological activity. These chemical substances are used as markers, in order to qualitatively and quantitatively standardise the extracts. The alcoholic extracts of Curcuma are chemically characterised in that they contain curcuminoids (curcumin, desmetoxicurcumin and bisdesmetxosicurcumin). The aqueous extract of Curcuma is characterised in that it does not contain curcuminoids, but a protein fraction and a polysaccharide fraction, in which ukonan A, B and C have been identified. The pharmacological effect is due to the total composition of the aqueous and/or alcoholic extract of Curcuma longa.

However, said markers (curcuminoids), may also be used alone in pharmaceutical composition showing their pharmaceutical activity.

PURPOSE OF THE INVENTION

The problem solved in one aspect of the invention is to provide a pharmaceutical composition for the treatment of the proliferative diseases on eukaryote cells, namely psoriasis, vitiligo, lichen, mycosis fungoides, atopic dermatitis, granulomma annulare, without adverse effects and clinically effective.

The solution found by the inventors is a pharmaceutical composition for topical administration comprising a water soluble Curcuma extract, which is obtainable by extraction of Curcuma rhizomes with means for solubilizating water-soluble compounds, and suitable excipients for topical administration, as such, emulgents, diluents, humectants, preservatives, pH adjusters and water.

An advantage of this aspect of the invention, as is shown in Example 1, is that after 7 or 14 days of treatment the psoriasis lesion there were not visible and there were no residual lesion, in addition all the patients tolerated well the treatment.

The association of the aqueous Curcuma extract with UVA favoured the product's activity, whitening the lesions after three days of treatment.

In one embodiment of the invention, the pharmaceutical composition comprises further an apolar Curcuma extract which is obtainable with means for extracting curcuminoids.

The advantage of said embodiment, according to Example 5, is that the patients shown an improvement in the lesion after the treatment with the pharmaceutical composition and visible light. No UV radiation is needed.

An other advantage of the embodiment is that Curcuma extract comprised in the pharmaceutical composition inhibited cell proliferation without altering the mithocondrial activity and they have no effect on protein synthesis, therefore the extract shown a cytostatic activity.

Further, the most important advantage is that in studies on eucaryote cells (human keratinocytes) the activated curcumin (present in apolar extracts) was found in the cytoplasm, therefore the nuclei is free from curcumin and the extract does not interact with nuclear DNA and mutagenic effects shown by other drugs, for instance psoralens, do not appear.

Further, both the aqueous extract and hydro alcoholic extract of Curcuma inhibited the secretion of cytokine IL-6 and/or IL-8 in human keratinocyes cultures with an activity similar to betametasone-17-valerate. The inhibition is increased after subjecting the cells to UV-A radiation.

Finally, the hydro alcoholic extract of Curcuma, consisting of an aqueous extract (without curcuminoids) and an apolar extract (characterized by curcuminoids), shown a greater photosensitization than curcumin after UVA radiation.

In a second aspect, the invention relates a process for obtaining the pharmaceutical composition for topical administration.

In a third aspect, the invention relates to the use as medicament of pharmaceutical composition above claimed.

Finally, the last aspect of the invention relates to the photosensitising activity of *Curcuma* extract and curcuminoids, wherein said cytokine production is IL-8 production or IL-6 production and said method results in inhibition of IL-8 production or IL-6 production, and wherein said proliferative disease is selected from the group consisting of psoriasis, lichen, atopic, dermatitis, granuloma annulare, mycosis fungoides or leukaemia for the treatment of proliferative diseases on eukaryote cells.

DETAILED DESCRIPTION OF THE INVENTION

The apolar extract of *Curcuma longa* can be obtained, according to Spanish Patent ES 2103689, by the extraction of the *Curcuma* rhizomes by macerating with alcohol (methanol, ethanol) at 50° C. for 24 hours and then removing the solvent at reduced pressure. The apolar extract of *Curcuma longa* is chemically characterised in that it contains curcuminoids. Alternatively, other extraction and/or purification methods known by an expert can be used, such as extraction with other organic solvents, extraction with solvents in a supercritical state, reflux extraction and steam current extraction. The extract can be purified by fractioned crystallisation, chromatography, liquid-liquid extraction, etc.

The aqueous extract of *Curcuma* can also be obtained by macerating with water for 24 hours at 50–70° C. and then removing the solvent at reduced pressure. The aqueous extract of *Curcuma longa* is chemically characterised in that it contains a protein fraction with a concentration around 20–30%, measured by the Pierce method, analysing the protein nitrogen, and a polysaccharide content (ukonan A, B and C) between 3–8%, without curcuminoids.

Alternatively, combinations of the two extracts can be used, obtaining hydro alcoholic extracts chemically characterised by the concentration of their markers (concentration of curcuminoids, proteins and polysaccharides).

The content of the markers can be measured by the methods described in the state of the art. The curcuminoids can be quantified by visible-ultraviolet spectrophotometry at 420 nm, the protein fraction can be quantified by the Pierce method, analysing the protein nitrogen and/or by liquid chromatography and the polysaccharide fraction is quantified by liquid chromatography.

Suitable excipients for topical administration are well-known in the art for manufacturing creams, gels, emulsions, liposomes, ointments. For instance, see Handbook of Pharmaceutical Excipients published by The Pharmaceutical Society of Great Britain (1986).

The studies carried out in vitro on human keratinocytes shown that the hydro alcoholic extract of *Curcuma longa* has shown a pharmacological activity greater than curcumin (greater proliferative activity, greater photosensitising activity, greater inhibition of cytokine secretion). These results support the view that vegetable extracts are drugs that are different than the molecules responsible for pharmacological activity, because the pharmacodynamics are different (absorption, distribution, action and elimination), and there could be synergic or anti-synergic effects between the different chemical species present in the extract. The hydro alcoholic extract of *Curcuma longa* has shown an antiproliferative activity similar to betametasone-17-valerate. This hydro alcoholic extract shown a significant decrease in the incorporation of 5-bromine-2'-deoxyuridin (BrdU) in the DNA of human keratinocyte cultures between concentrations of 5 µg/ml and 50 µg/ml of extract. This effect is similar to that of betametasone-17-valerate.

Both the aqueous extract of *Curcuma* and the hydro alcoholic extract of *Curcuma longa* have inhibited the secretion of cytokine IL-6 and/or IL-8 in human keratinocyte cultures with an activity similar to betametasone-17-valerate. This inhibition is increased after subjecting the cells to ultraviolet A radiation.

The aqueous and hydro alcoholic extracts of *Curcuma* have been seen to inhibit cell proliferation without altering the mitochondrial activity, and the extracts have no effect on protein synthesis. The extract therefore shows cytostatic activity.

On the other hand, the hydro alcoholic extracts show photosensitising activity and can therefore be used in proliferative diseases such as psoriasis, vitiligo, lymphomas, mycosis fungoides, etc., instead of psoralens.

In studies carried out on eucaryote cells (human ketinocytes) with *Curcuma longa* extracts, the activated curcumin has been found in the cytoplasm. Therefore, the nucleus is free from curcumin, the extract does not interact with the nuclear DNA and the secondary, and mutagenic effects produced by psoralens do not appear.

The hydro alcoholic extract (10% curcuminoids, 18% protein fraction, 3% polysaccharides) of *Curcuma* shows a greater photosensitising activity after UVA radiation than curcumin.

Therefore, a smaller amount of the drug is best for a greater photosensitising activity (lower percentage of BrdU incorporated).

|  | % incorporation | | | |
| --- | --- | --- | --- | --- |
|  | 80 | 60 | 40 | 20 |
| Extract (ng) | 2000 | 4000 | 5000 | 6000 |
| Curcumin equivalent (ng) | 200 | 400 | 500 | 600 |
| Curcumin (ng) | 600 | 800 | 1000 | 1200 |

To produce the same level of photosensitising as *Curcuma* extracts, doses of 10 ng/ml of psoralen is required, as with this dose toxic and mutagenic effects are produced.

The administration of a topical pharmaceutical composition comprising an aqueous extract of *Curcuma longa* at 2%, and one tablet a day with 100 mg of aqueous extract with pharmaceutically acceptable excipients has been seen to be clinically effective in different types of psoriasis, and these effects are increased after radiation with ultraviolet A light. There are no side effects, as is the case for corticoids.

22 patients with different types of psoriasis were studied: Guttate, Vulgar, Inverse, Palmo-plantar, Pustular. They were without any psoriasis treatment (retinoids, corticoids, etc.) for 15 days. The topical composition with aqueous *Curcuma* extract was then applied and a tablet was administered every 12 days. The composition was tolerated perfectly by all the patients and no patient had to cease treatment because of cutaneous or systemic adverse reactions react to conventional treatments, all the patients responded to the treatment.

In the vulgar psoriasis, the plaque was reduced after administration. Fissured and/or ulcerated pustular psoriasis scarred quickly. An antiseptic and drying effect was observed in the inverse psoriasis.

The association of the aqueous *Curcuma* extract with UVA favoured the product's activity, whitening the lesions after three days of treatment.

The hydro alcoholic (10% curcuminoids, 18% protein fraction, 3% polysaccharides) extract of *Curcuma* has shown photosensitising activity with visible light, inhibiting the percentage of BrdU incorporated into the DNA after radiation with visible light in human keratinocyte cultures.

The administration of the pharmaceutical composition which the active ingredient is the hydro alcoholic extract of *Curcuma longa* at 2% with pharmaceutically acceptable excipients has been shown to be clinically effective in the different types of psoriasis that did not respond to treatment with corticoids or with PUVA. After 15 days of treatment with composition comprising an hydro alcoholic extract of *Curcuma longa*, the erythema, the infiltration and the scaling disappeared. The effects were greater after radiation with visible light and there were no side effects, unlike with the use of psoralens and ultraviolet light.

EXAMPLES

Example 1

Effect of Aqueous *Curcuma* Extract on Psoriasis

Quantitative Composition:

| | |
|---|---|
| Aqueous Curcuma extract | 2% |
| Greasy phase | 27% |

-continued

| | |
|---|---|
| Emulgents | 47% |
| Humectants | 20% |
| Preservatives | 1% |
| pH adjusters | 1% |
| Water | csq |

* Content in proteins no less than 15%, content in polysaccharides no less than 4%.

22 patients diagnosed with psoriasis were studied, distributed by age and sex.

| Sex | Age | Type of psoriasis |
|---|---|---|
| F | 12 | Guttate |
| F | 22 | Vulgar |
| F | 37 | Palmo-plantar |
| M | 24 | Vulgar |
| M | 48 | Vulgar |
| F | 51 | Inverse |
| F | 27 | Palmo-plantar |
| M | 19 | Vulgar |
| M | 57 | Palmo-plantar |
| M | 61 | Inverse |
| F | 46 | Palmo-plantar |
| M | 6 | Pustular |
| M | 16 | Vulgar |
| F | 32 | Vulgar |
| F | 39 | Pustular |
| F | 41 | Vulgar |
| M | 31 | Palmo-plantar |
| F | 13 | Guttate |
| F | 3 | Vulgar |
| F | 51 | Vulgar |
| F | 60 | Inverse |
| F | 19 | Palmo plantar |

Criteria for Inclusion:

Patients clinically or histologically diagnosed with psoriasis.

They had no other disease.

They did not receive treatment for psoriasis.

Protocol:

The 22 patients went for 15 days without treatment of any kind, emollients, corticoids, retinoids, fatty acids Patients were instructed to apply the formula 3 times a day with a light massage and take 1 tablet every 12 hours.

Results:

The topical composition presented no irritation or contact reaction.

The cases of guttate psoriasis evolved in the same way. Their lesions were not very scaly but very erythematous. After 7 days of treatment there were no scaled and the erythema was minimal. After 14 days the lesions were not visible. There were no residual pigmentation lesions.

4 of the 6 cases of psoriasis palmo-plantar had the palms more evidently affected, with scaly lesions and significant fissuration. After 7 days of treatment the fissuration, painful for the patients, had disappeared and been replaced by an erythematous lesion with badly defined borders with practically no scales. After 14 days, the lesions had been reduced to a slightly erythematous macula on skin with normal characteristics. The plantar lesions presented an important hyperkeratosis with fissuration and were more resistant to treatment, obtaining results after 14 days, with scarred fissures.

In the two patients with pustular psoriasis, the lesions scarred after a week of treatment and the scales disappeared after 14 days of treatment.

In the patients with inverse psoriasis, the lesions were slightly scaly and intensively erythematous with an eroded surface. Cultures were prepared and they were contaminated with *Candidas*. After 7 days of treatment, scale shedding had ceased and the erythema was reduced. After 14 days of treatment only a slightly erythematous macula was observed.

The most studied case was vulgar psoriasis, because it represented the largest number of patients. The lesions in the trunk area presented considerable infiltration and peripheral scale shedding. Hyperkeratosis was predominant on the articulations. After 7 days of treatment the infiltration and the erythema was drastically reduced. After 14 days reaction was positive on both the trunk and the articulations, and very slightly erythematous lesions were observed on the trunk and slightly scale-shedding lesions on elbows and knees.

In patients with palmo-plantar psoriasis treated with PUVA, the fissures and scale shedding disappeared 72 hours after treatment. In patients with vulgar psoriasis treated with PUVA, the lesions showed no infiltration and scale shedding after 2 sessions.

Example 2

Effects of *Curcuma longa* Extracts on the Secretion of Interleukines IL-6 and IL-8 in Human Keratinocyte Cultures Culture of the HaCat Line:

The HaCat line is an immortalised line of normal human keratinocytes. These cells grow in a culture medium consisting of Hanks liquid to which 5% of foetal bovine serum and 2% of penicillin-streptomycin is added at 37° C. in a $CO_2$ atmosphere.

Determination of the Interleukines.

After 48 hours of incubation with or without radiation, the supernatant of the cultures is taken to measure the IL-6 and IL-8 using an ELISA test kit. The minimum detection for each test is 3.13 pg/ml for the IL-6 and 31.0 pg/ml for the IL-8.

Cell Radiation.

The cells were radiated by an UVA/UVB lamp with a UVA range of 340–390 nm and a UVB range of 290–310, with no UVC. The radiation dose was 150 mJ/cm. To avoid toxic products from the culture media from forming, PBS free calcium and magnesium ions were changed before radiation.

Results:

The hydro alcoholic and aqueous *Curcuma* extracts, at doses of 50 µg/ml, inhibited the secretion of interleukines IL-6 and IL-8 after radiation with UVB light in a similar way.

Example 3

Effect of *Curcuma longa* Extracts on the Incorporation of BrdU in the DNA of Human Keratinocytes Culture of the HaCat Line:

The HaCat line is an immortalised line of normal human keratinocytes. These cells grow in a culture medium consisting of Hanks liquid to which 5% of foetal bovine serum and 2% of penicillin-streptomycin is added at 37° C. in a $CO_2$ atmosphere.

Incorporation of BrdU:

To determine the replication rate, the cells were grown in microplates at a density of 2*10 cells per matrix. After 24 hours of treatment the media was renewed and the cultures were incubated for 24 hours at 37 DEG C. with different concentrations of the extracts and betametasone-17-valerate with a concentration of 10 µg/ml. Parallel controls were carried out with the solvent (ethanol 0.1%). The incorporation of BrdU was determined with the ELISA test.

Figure 1:
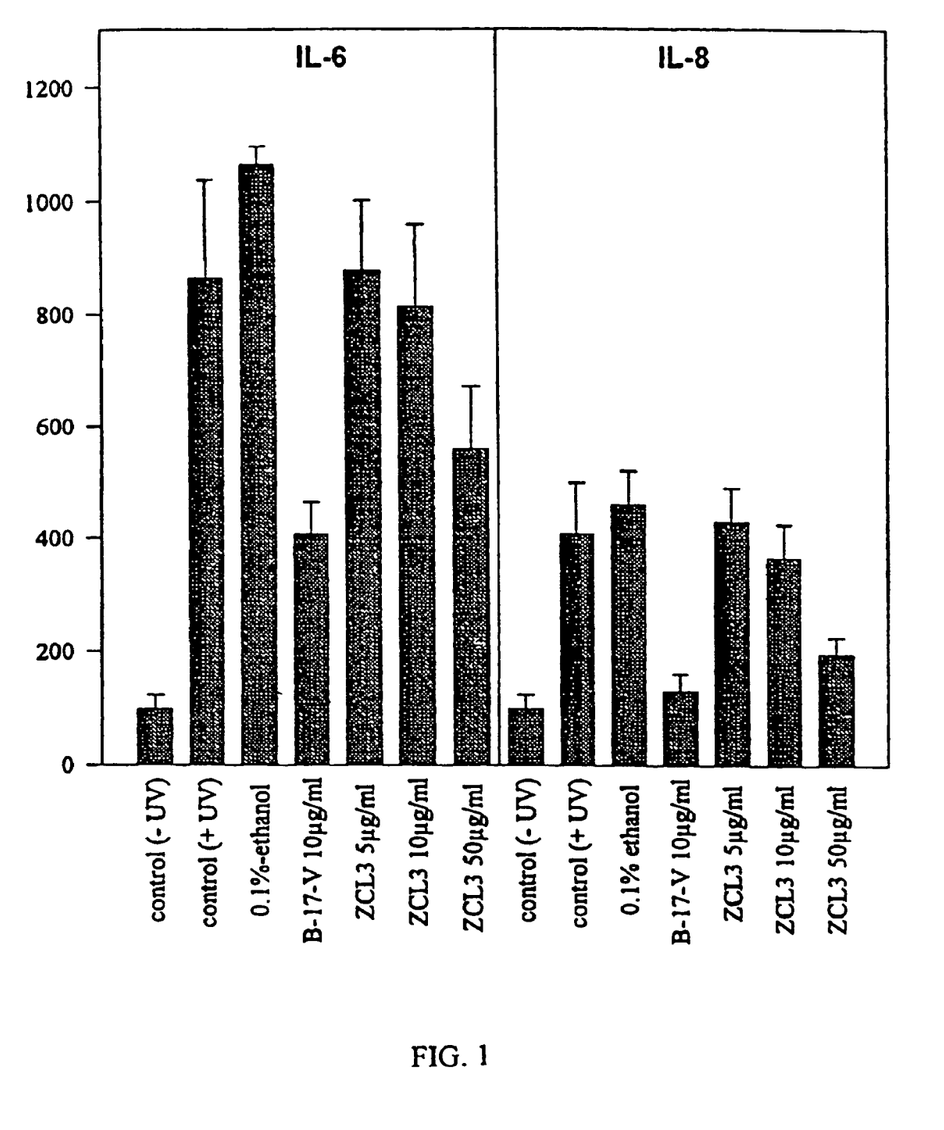
FIG. 1 shows inhibition of the secretion of IL-6 and IL-8 after ultraviolet light radiation of aqueous *Curcuma* extract (ZCL3) and betametasone-17-valerate (B-17-V).
Figure 2:
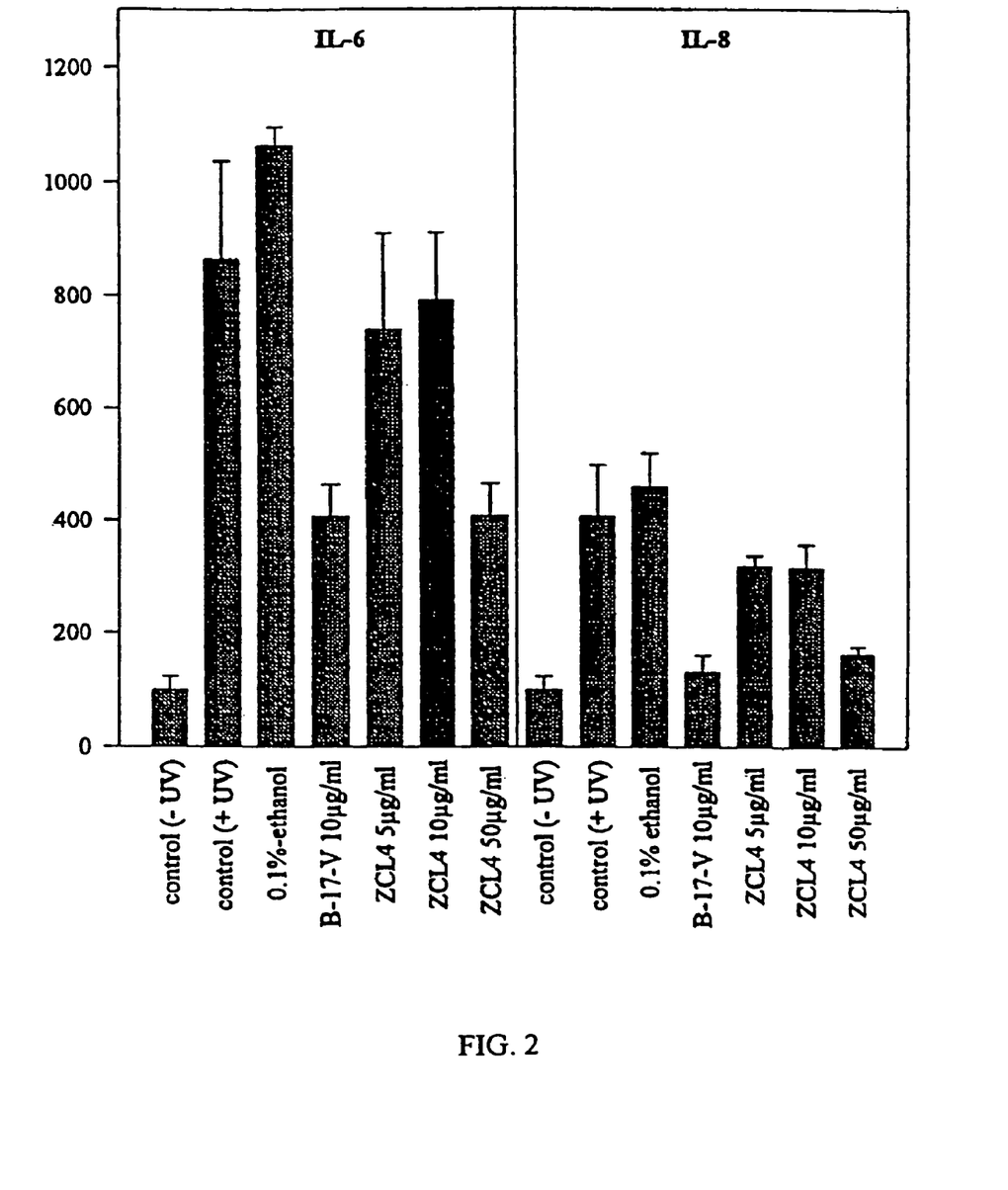
FIG. 2 shows inhibition of the secretion of IL-6 and IL-8 after ultraviolet light radiation of hydro alcoholic *Curcuma* extract (ZCL4) and betametasone-17-valerate (B-17-V).
Figure 3:
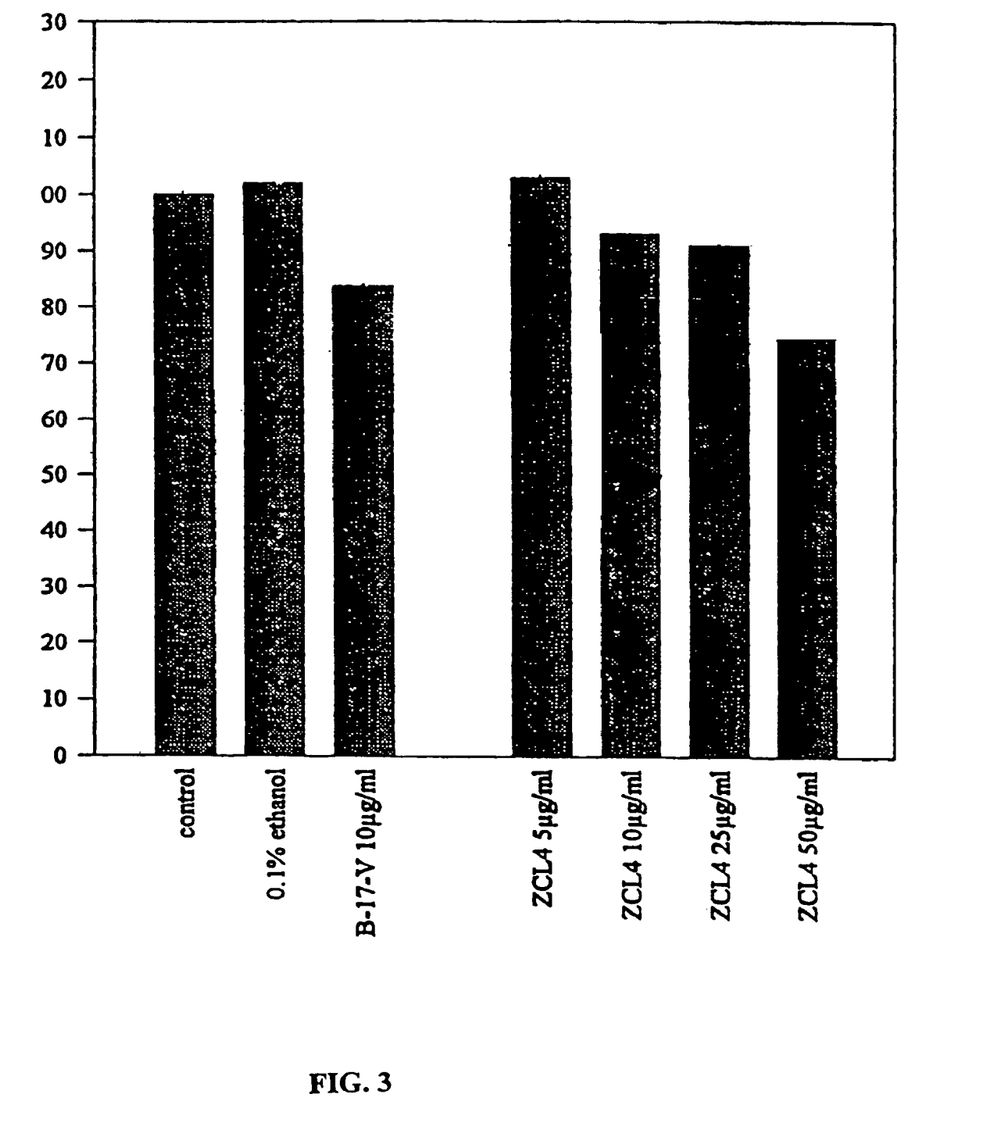
FIG. 3 shows incorporation of BrdU of hydro alcoholic *Curcuma* extract (ZCL4) and betametasone-17-valerate (B-17-V).
Figure 4:
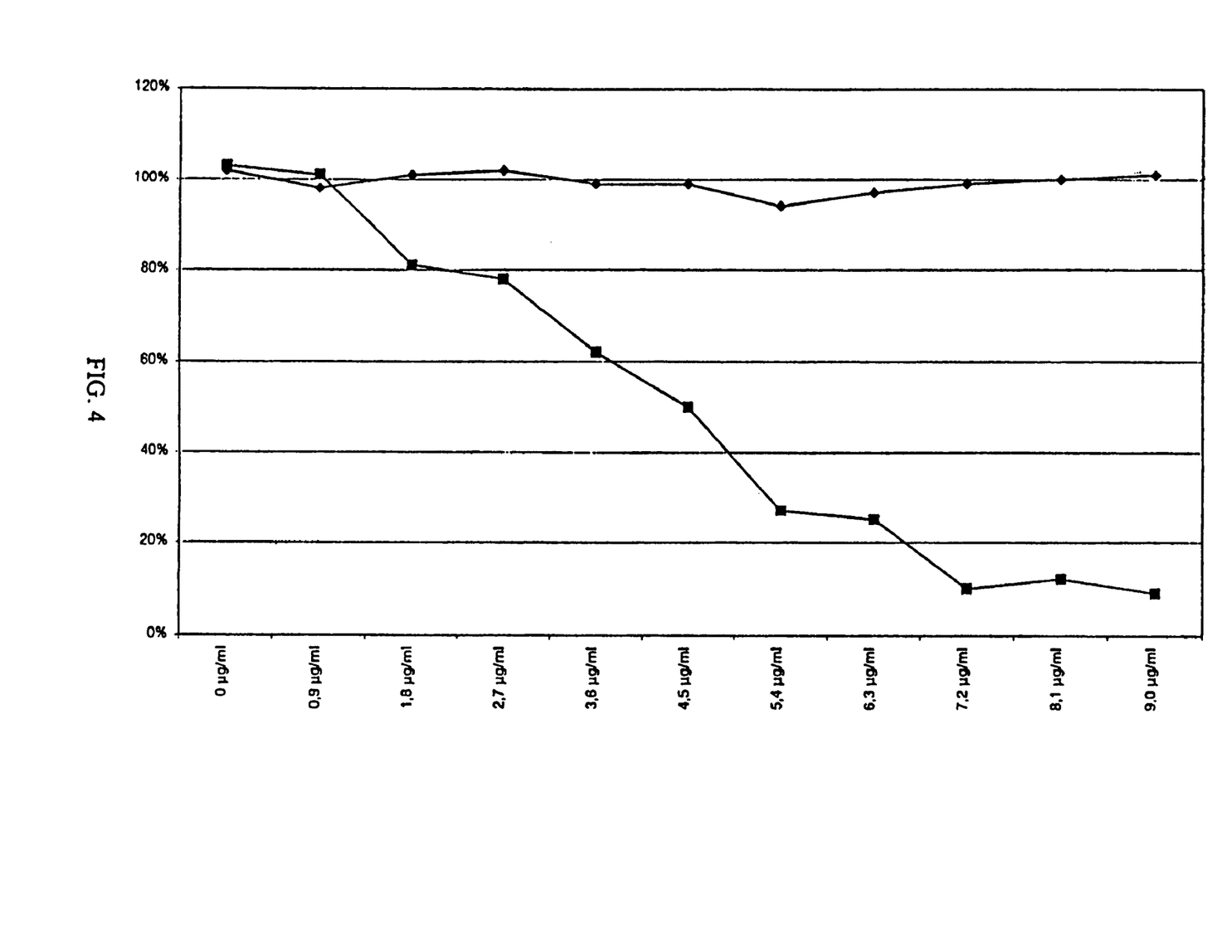
FIG. 4 shows the effect of aqueous *Curcuma* extract (ZCL3) on the incorporation of BrdU in the DNA after UV radiation. Photosensitive capacity.
Figure 5:
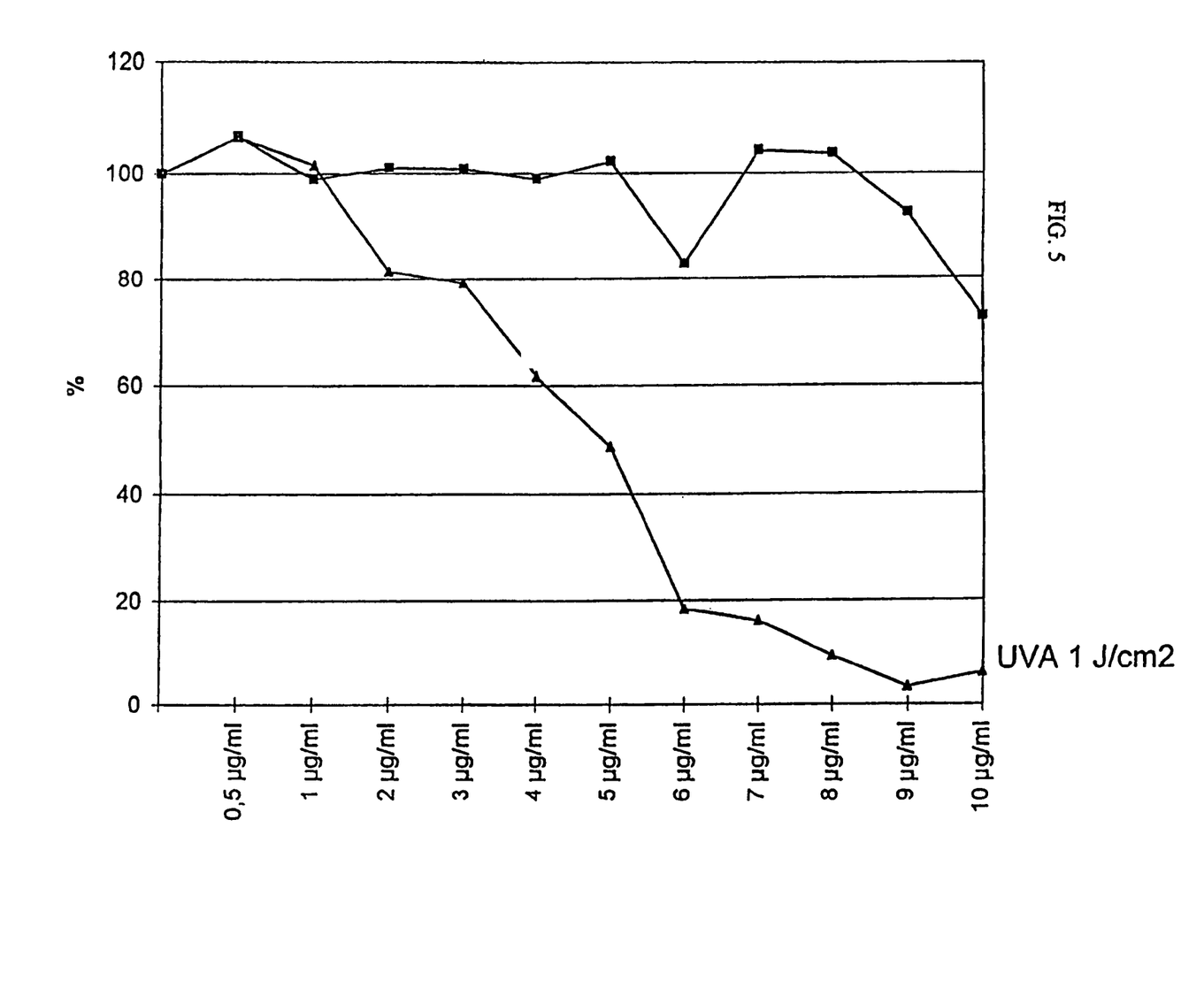
FIG. 5 shows the effect of hydro alcoholic *Curcuma* extract (ZCL4) on the incorporation of BrdU in the DNA after UV radiation. Photosensitive capacity.
Figure 6:
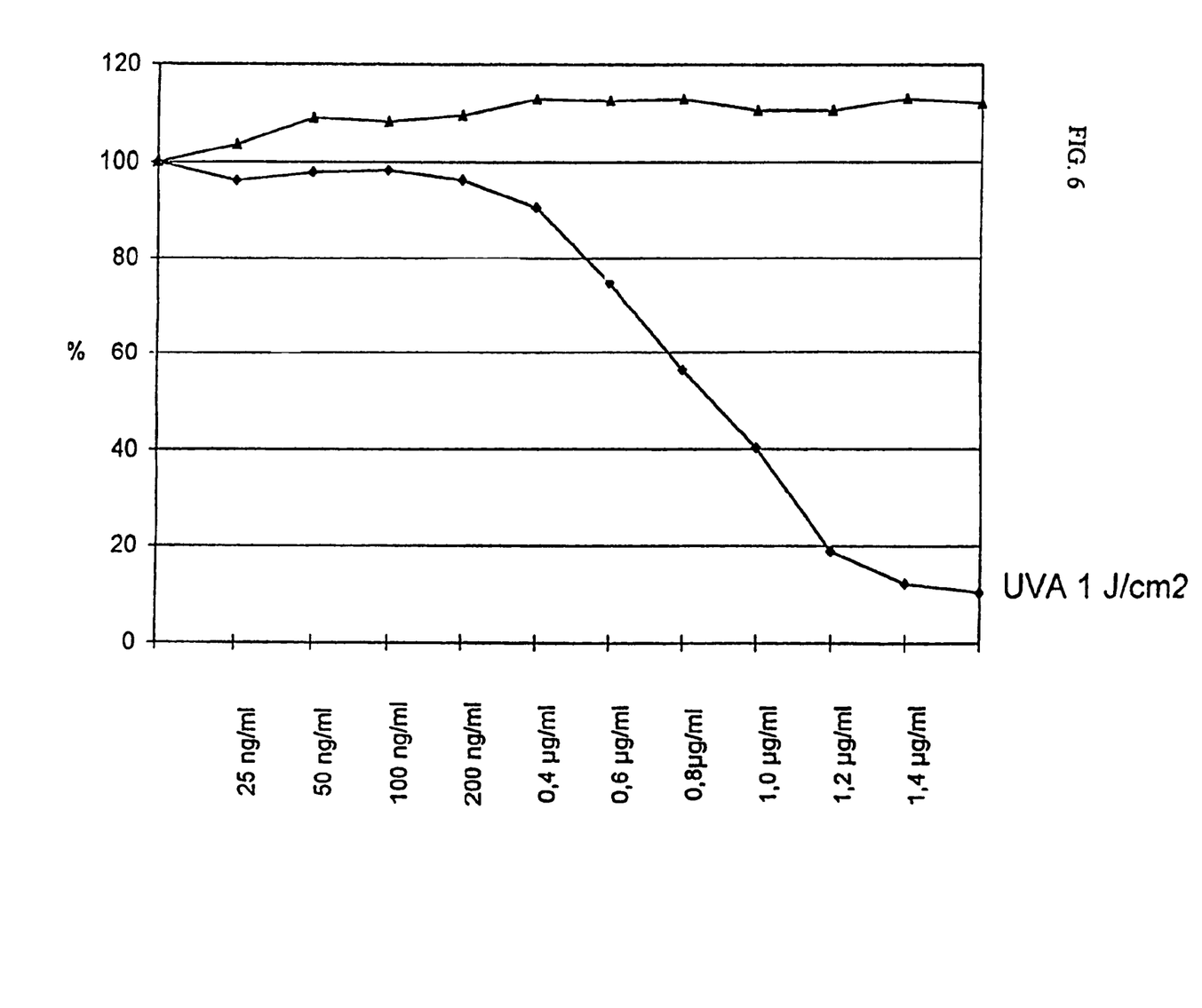
FIG. 6 shows the effect of curcumin on the incorporation of BrdU in the DNA after UV radiation. Photosensitive capacity.
Figure 7:
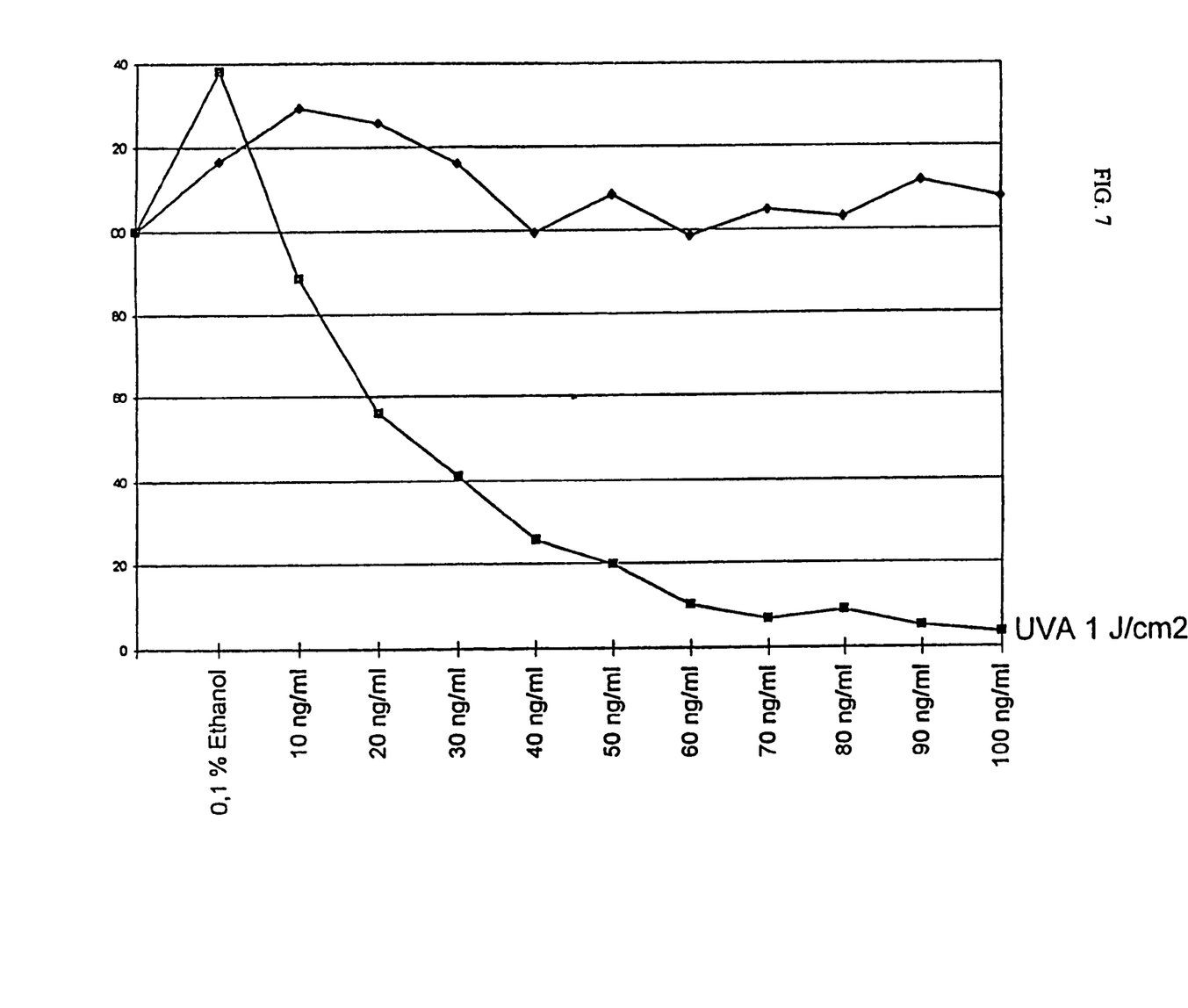
FIG. 7 shows the effect of psoralen on the incorporation of BrdU in the DNA after UV radiation. Photosensitive capacity.

Results:

The incubation of the cells with 50 µg/ml of hydro alcoholic extract leads to a significant decrease in the incorporation with BrdU. The hydro alcoholic extract, a combination of the aqueous and alcoholic extract of *Curcuma longa*, shown an anti-proliferative activity similar to betametasone-17-valerate (FIG. 3).

Example 4

Effect of *Curcuma longa* Extracts on the Incorporation of BrdU in the DNA of Human Keratinocytes after Radiation with Ultraviolet Light Culture of the HaCat Line:

The HaCat line is an immortalised line of normal human keratinocytes. These cells grow in a culture medium consisting of Hanks liquid to which 5% of foetal bovine serum and 2% of penicillin-streptomycin is added at 37° C. in a $CO_2$ atmosphere.

Incorporation of BrdU:

To determine the replication rate, the cells were grown in microplates at a density of 2*10 cells per matrix. After 24 hours of treatment, the media was renewed and the cultures were incubated for 24 hours at 37° C. with different concentrations of the extracts and different concentrations of the curcumin and psoralen. Parallel controls were carried out with the solvent (ethanol 0.1%). The incorporation of BrdU was determined with the ELISA test.

The cells were radiated with UVA light at an intensity of 1 J/cm and the incorporation of BrdU was then analysed.

Results:

The hydro alcoholic extract of *Curcuma longa* with 10% curcuminoids, 18% proteins and 3% polysaccharide fraction, shown a photosensitising activity greater than curcumin after radiation with UVA light, that is less percentage of incorporation.

Aqueous *Curcuma longa* extract has photosensitising properties.

To produce the same level of photosensitising as *Curcuma* extracts, toxic doses of psoralen (10 ng/ml) have to be used (FIGS. 4, 5, 6, 7).

Example 5

Effect of the Hydro Alcoholic Extracts of *Curcuma longa* on Psoriasis with Visible Radiation Quantitative Composition of the Pharmaceutical Product:

| | |
|---|---|
| Hydro alcoholic Curcuma extract* | 2% |
| Greasy phase | 27% |
| Emulgents | 47% |
| Humectants | 20% |
| Preservatives | 1% |

-continued

| | |
|---|---|
| pH adjusters | 1% |
| Water | csq |

*Equivalent to 10% of curcuminoids, 18% of proteins.

8 patients who were affected and diagnosed with and treated for different types of psoriasis: Guttate, Vulgar, Inverse and Palmo-plantar. The previous treatment consisted of the application of corticoid creams, PUVA sessions (around 14 sessions per patient) and in some cases retinoids therapy. The distribution of the patients by sex, age and type of psoriasis was as follows.

| Age | Sex | Type of psoriasis |
|---|---|---|
| 9 | Female | Palmar |
| 6 | Female | Guttate |
| 31 | Male | Vulgar |
| 46 | Female | Vulgar |
| 19 | Female | Palmo-plantar |
| 56 | Female | Vulgar & palmo-plantar |
| 14 | Female | Guttate |
| 28 | Male | Inverse |

The composition with the hydro alcoholic extract was applied to the lesions and after 10 minutes, the patients were radiated with a 440 nanometers lamp for three minutes. Sessions were weekly. The erythema, the infiltration and the scale shedding were evaluated after 48 hours, 5 days and 15 days.

The results obtained were:

| Type of psoriasis | Erythema | Infiltration | Scale shed |
|---|---|---|---|
| Day 0 | | | |
| Palmar | ++ | +++ | +++ |
| Guttate | ++ | +++ | ++ |
| Vulgar | ++ | ++ | +++ |
| Palmo plantar | + | +++ | +++ |
| Inverse | +++ | ++ | + |
| Day 2 | | | |
| Palmar | ++ | ++ | ++ |
| Guttate | ++ | ++ | + |
| Vulgar | + | ++ | +++ |
| Palmo plantar | + | + | ++ |
| Inverse | ++ | ++ | + |
| Day 5 | | | |
| Palmar | ++ | + | + |
| Guttate | + | + | − |
| Vulgar | + | + | + |
| Palmo plantar | + | − | ++ |
| Inverse | − | + | − |
| Day 15 | | | |
| Palmar | + | − | − |
| Guttate | + | − | − |
| Vulgar | − | − | + |
| Palmo plantar | − | − | + |
| Inverse | − | − | − |

Wherein,
+++ means intense
++ means moderate
+ means slight
− means negative

An improvement was observed in the erythema, infiltration and skin shedding after treatment with *Curcuma longa* extract and visible light.

Example 6

Effect of *Curcuma longa* Extracts on the Incorporation of BrdU in the DNA of Human Keratinocytes after Radiation with Visible Light Culture of the HaCat Line:

The HaCat line is an immortalised line of normal human keratinocytes. These cells grow in a culture medium consisting of Hanks liquid to which 5% of foetal bovine serum and 2% of penicillin-streptomycin is added at 37° C. in a $CO_2$ atmosphere.

Incorporation of BrdU:

To determine the replication rate, the cells were grown in microplates at a density of 2*10 cells per matrix. After 24 hours of treatment, the media was renewed and the cultures were incubated for 24 hours at 37° C. with different concentrations of the extracts and different concentrations of the curcumin and psoralen. Parallel controls were carried out with the solvent (ethanol 0.1%). The incorporation of BrdU was determined with the ELISA test.

The cells were radiated with visible light using an actinium lamp with a spectrum of 400–550 nm (maximum at 450 nm).

Figure 8:
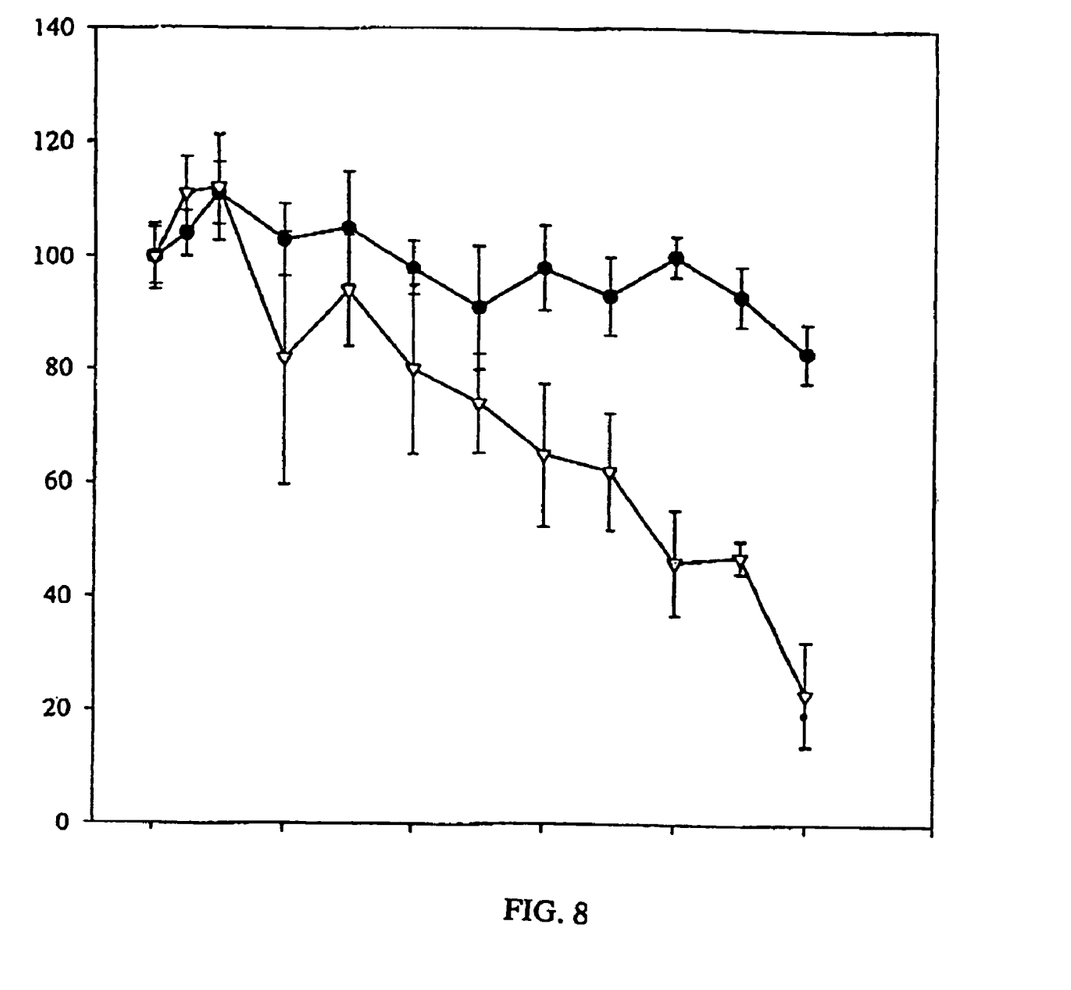
FIG. 8 shows the effect of the hydro alcoholic extract of *Curcuma longa* on the incorporation of BrdU in the DNA of human keratinocytes with visible light radiation (450 nm) and without radiation, with the concentration in μg/ml of extract represented on abscissas and the percentage of BrdU incorporation on ordinates. Photosensitising capacity with visible light.

Results:

The hydro alcoholic extract of *Curcuma longa* with 10% of curcuminoids, 18% of proteins and 3% of polysaccharide fraction shown a decrease in DNA synthesis. The maximum inhibition of BrdU incorporation was at concentrations of 10 μg/ml of extract (FIG. 8).

While the invention has been described in detail and with reference to specific embodiments thereof, it will be apparent to one skilled in the art that various changes and modifications can be made therein without departing from the spirit and scope thereof.

What is claimed:

1. A method for treating a mammal having a proliferative disease characterized by skin inflammation comprising topically administrating to said mammal an effective amount of a pharmaceutical composition comprising an aqueous *Curcuma* extract, and then subjecting said mammal to ultraviolet radiation.

2. The method of claim 1, wherein said proliferative disease is selected from the group consisting of psoriasis, lichen, atopic dermatitis, granuloma annulare, and mycosis fungoides.

3. The method of claim 1, further comprising orally administering to said mammal an effective amount of an aqueous *Curcuma* extract.

4. The method of claim 1, wherein said pharmaceutical composition comprises a 2% *Curcuma longa* aqueous extract.

5. The method of claim 1, wherein said pharmaceutical composition is administered for 7 or 14 days.

6. The method of claim 3, wherein 100 mg/day of an aqueous *Curcuma* extract is orally administered.

7. The method of claim 1, wherein said ultraviolet radiation is ultraviolet A.

8. The method of claim 1, wherein said mammal has psoriasis.

9. The method of claim 8, wherein said method results in a reduction of skin lesions.

10. The method of claim 1, wherein said proliferative disease is characterized by production of IL-8 or IL-6.

11. The method of claim 1, wherein said *Curcuma* extract is an extract of *Curcuma longa* rhizomes.

12. A method for treating a mammal having a proliferative disease characterized by skin inflammation comprising:
   topically administrating to said mammal an effective amount of a pharmaceutical composition comprising a hydro alcoholic *Curcuma* extract,
   irradiating said mammal with a lamp that radiates visible light having a spectrum of 400–550 nanometers, and
   subjecting said mammal to ultraviolet radiation.

13. The method of claim 12, wherein said proliferative disease is selected from the group consisting of psoriasis, lichen, atopic dermatitis, granuloma annulare, and mycosis fungoides.

14. The method of claim 12, wherein said extract comprises a 2% *Curcuma longa* hydro alcoholic extract.

15. The method of claim 12, wherein said method is performed weekly.

16. The method of claim 12, wherein said mammal has psoriasis.

17. The method of claim 15, wherein said method results in a reduction of skin lesions.

18. The method of claim 12, wherein said *Curcuma* extract is an extract of *Curcuma* longa rhizomes.

* * * * *